United States Patent [19]
Boomgaarden

[11] Patent Number: 5,863,010
[45] Date of Patent: Jan. 26, 1999

[54] APPARATUS FOR ROUTING RESILIENT CABLE ACROSS ROTARY JOINT

[75] Inventor: Jonathan C. Boomgaarden, Waukesha, Wis.

[73] Assignee: General Electric Company, Milwaukee, Wis.

[21] Appl. No.: 951,891

[22] Filed: Oct. 16, 1997

[51] Int. Cl.$^6$ ................................................. H01R 39/00
[52] U.S. Cl. ............................................. 242/388; 439/15
[58] Field of Search ................................. 242/388, 388.1; 439/13, 15

[56] References Cited

U.S. PATENT DOCUMENTS

| | | | |
|---|---|---|---|
| 3,412,951 | 11/1968 | Ober | 242/388 |
| 4,468,070 | 8/1984 | Yasuoka | 439/13 |
| 5,046,951 | 9/1991 | Suzuki | 439/15 |
| 5,098,028 | 3/1992 | Ida et al. | 242/388.6 |
| 5,149,273 | 9/1992 | Bannai et al. | 439/15 |
| 5,174,515 | 12/1992 | Meier | 242/388 |
| 5,219,460 | 6/1993 | Kato et al. | 439/15 |
| 5,224,871 | 7/1993 | Ida et al. | 439/15 |
| 5,240,092 | 8/1993 | Eachus | 439/13 |
| 5,252,085 | 10/1993 | Kato et al. | 439/15 |
| 5,259,775 | 11/1993 | Kubota et al. | 439/15 |
| 5,277,604 | 1/1994 | Ida et al. | 439/15 |
| 5,304,071 | 4/1994 | Bannai et al. | 439/15 |
| 5,314,344 | 5/1994 | Ida et al. | 439/15 |
| 5,382,172 | 1/1995 | Klier et al. | 439/15 |
| 5,547,144 | 8/1996 | Sakamoto et al. | 439/15 |
| 5,593,310 | 1/1997 | Kawamoto et al. | 439/15 |

*Primary Examiner*—John P. Darling
*Attorney, Agent, or Firm*—James O. Skarsten; Christian G. Cabou; Phyllis Y. Price

[57] ABSTRACT

Apparatus for routing a resilient cable of specified length, such as an electric power transmission cable, across a rotary joint between first and second members, wherein the first member is supported for rotation with respect to the second member. The apparatus includes a first guide element disposed to rotate with the first member, for guiding a first component or portion of a cable along a first arcuate path of specified radius, the length of the first cable component disposed to vary as the first member rotates. The apparatus further includes a second guide element, in fixed relationship to the second member, for guiding a second component of the cable along a second arcuate path, the length of the second cable component disposed to vary in inverse relation to the length of the first cable component. The first and second guide elements are mounted in spaced-apart relationship, to provide a spacing therebetween which is selected to form a third component of the cable, extending between the first and second cable components, into a loop of specified configuration. The first and second guide elements are provided with first and second annular channels, respectively, each arcuate cable path lying along a portion of one of the annular channels.

14 Claims, 5 Drawing Sheets

APPARATUS FOR ROUTING RESILIENT CABLE ACROSS ROTARY JOINT

BACKGROUND OF THE INVENTION

The invention disclosed and claimed herein generally pertains to apparatus for routing or directing a cable across a rotary joint, that is, a joint between first and second members wherein the first member is supported for rotation with respect to the second member. More particularly, the invention pertains to apparatus of such type for use with cables which are very resilient, such as high voltage electric cables having rubberized insulation. Even more particularly, the invention pertains to apparatus of the above type which can simultaneously route a plurality of cables across the rotary joint.

It is frequently necessary in X-ray equipment to provide means for moving the X-ray tube, or other X-ray source, through multiple degrees of freedom. The user of the equipment is thereby enabled to move the tube into virtually any position desired, in the course of performing X-ray exams. In one class of X-ray equipment, referred to as mobile or portable X-ray systems, the X-ray tube and collimator are mounted by means of gimbals which allow them to rotate about two intersecting axes. The gimbals are joined to the end of a telescoping horizontal arm which can be extended radially. The arm is supported on a carriage which is moveable along a column, and the column is rotatable with respect to a base or the like. By providing a tube mounting arrangement of such type, the X-ray tube can be positioned as required, at any position within its range of motion. Mobile X-ray systems provided with such tube mounting arrangement are exemplified by a product of the General Electric Company, the assignee herein, which is known as the AM-4 X-ray Unit. This product comprises an X-ray machine mounted on a wheeled carriage and provided with a drive motor and steering controls. The unit can thus be easily moved, for example, from one room to another in a hospital. Mobile systems of this type are of increasing interest to hospitals and other X-ray users, and are, accordingly, of increasing commercial importance.

A difficulty which arises, in tube mounting arrangements of the above type, is that it is necessary to attach electric cables to the X-ray tube in order to generate X-rays. Generally, two cables are required, one for the tube anode and the other for the tube cathode. These cables must be routed so that they do not impede the positioning of the X-ray source. In addition, they must not extend too far from the equipment. Otherwise, they may create a hazard when the equipment is moved, or may become snagged on an obstruction and be damaged. The traditional solution to this problem has been to provide mounting points for the cables, and to leave loops of loose cable between the mounting points to accommodate the motion of respective components of the tube mounting arrangement.

In mobile X-ray systems of the type described above, the voltage required for the tube, which is on the order of 75,000 volts, is generally provided by an X-ray generator mounted on the base. Thus, the cables extending between the generator and the X-ray tube, mounted on the column, are coupled across a rotary joint between the base and column, as referred to above. It is desirable, in X-ray systems of the above type, to allow the column to rotate through an arc of 270° in a clockwise direction, from a zero angle reference, and also to rotate through an arc of 270° in a counter clockwise direction therefrom. Thus, the column must be able to rotate through a total angle of 540° relative to the base. In the conventional solution referred to above, enough extra cable must be provided to enable the cable to wrap around and around the column, as the column is rotated through its range. However, when the column is rotated into a position which is near or at its zero angle reference position, the extra cable will become loose or slack and hang in loops. If the slack cable is accessible to persons or objects proximate to the X-ray system, hazards of the type referred to above will be created. However, providing structure to protectively enclose the slack or excess cable would add cost to the X-ray system, and could interfere with its operation.

SUMMARY OF THE INVENTION

The invention is generally directed to apparatus for routing a resilient cable of specified length across a rotary joint between first and second members, wherein the first member is supported for rotation with respect to the second member. The apparatus comprises a first guide means, disposed to rotate with the first member, for guiding a first component or portion of the cable along a first arcuate path having a specified radius, the length of the first cable component disposed to vary as the first member rotates. The apparatus further comprises a second guide means, in fixed relationship to the second member, for guiding a second component of the cable along a second arcuate path having a specified radius, the length of the second cable component disposed to vary in inverse relation to the length of the first cable component. Means are provided for mounting the first and second guide means in spaced-apart relationship, to provide a spacing therebetween which is selected to form a third component of the cable, extending between the first and second cable components, into a loop of specified configuration. The apparatus also includes means for joining one end of the cable in fixed relationship with the first guide means, and for joining the opposing end of the cable in fixed relationship with the second guide means.

In a preferred embodiment, the first and second guide means comprise first and second arcuate channels, respectively, each of the arcuate channels having a specified radius and an open side. The mounting means comprises means for joining the first and second arcuate channels to the first and second members, respectively, the open sides of the arcuate channels being oriented toward each other. The first and second arcuate channels are of sufficient dimensions to accommodate the maximum lengths of the first and second cable components, respectively. The loop is guided along a path of movement between the first and second arcuate channels as the first member rotates, the loop substantially maintaining its specified configuration. A port is formed in each of the arcuate channels, each of the ports being sized to allow a corresponding end of the cable to pass therethrough.

In another useful embodiment, the first and second arcuate channels comprise segments of first and second annular channels, respectively, the first and second annular channels being respectively joined to the first and second members, and maintained in spaced-apart relationship with one another. Such embodiment may be used to route a plurality of resilient cables across a rotary joint, such as the anode and cathode cables of a mobile X-ray unit of the type described above. In such arrangement each cable occupies a different arcuate segment of the first and second annular channels, at a given time. However, the invention is by no means limited to such use.

OBJECTS OF THE INVENTION

An object of the invention is to provide improved apparatus for coupling or routing a cable across a rotary joint.

Another object is to provide apparatus of the above type which is particularly well suited for use with a resilient cable or the like, such as a coaxial cable employed to transmit electric power of very high voltage, and which includes a substantial amount of rubber or rubberized material for insulation.

Another object is to provide an apparatus of the above type, wherein the amount of additional or excess cable needed to cross the rotary joint is minimized.

Another object is to provide apparatus of the above type, wherein the section of the cable which is proximate to the rotary joint is substantially enclosed or shielded by the apparatus, to avoid interference with nearby persons or objects.

Another object is to provide apparatus of the above type which is particularly well suited for transmitting high voltage electric power across a rotary joint.

Another object is provide apparatus of the above type which is particularly well suited for use with mobile X-ray equipment having an X-ray tube supportably mounted on a rotatable column or other member.

These and other objects and advantages of the invention will become more readily apparent from the following description, taken together with the accompanying drawings.

DETAILED DESCRIPTION OF THE PREFERRED EMBODIMENT

Figure 1:
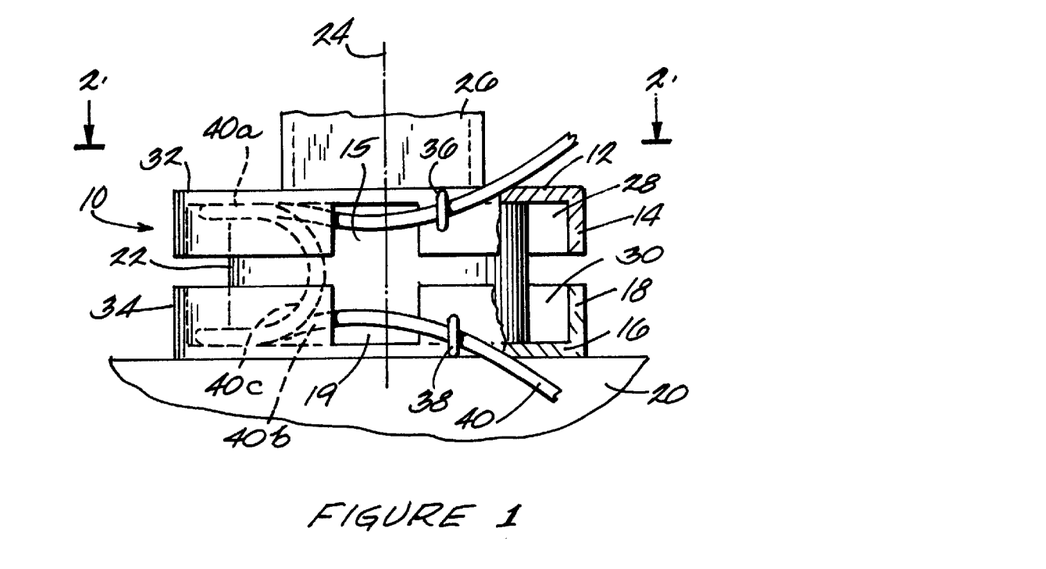
FIG. 1 is a perspective view with a section broken away showing an embodiment of the invention.

Referring to FIG. 1, there is shown cable routing apparatus 10 constructed in accordance with the invention. Apparatus 10 includes a circular upper plate 12, having a cylindrical wall 14 fixably joined to its circumference or outer edge. Apparatus 10 further includes a circular lower plate 16, substantially identical to plate 12 and likewise having a cylindrical wall 18, substantially identical to wall 14, fixably joined to its circumference. Lower plate 16 is fixably mounted upon a generalized horizontal supporting member 20 so that the cylindrical wall 18 extends upwardly from plate 16. Upper plate 12 is supported in spaced-apart relationship with lower plate 16 by means of a cylindrical drum 22, plate 12 being oriented so that its cylindrical wall 14 extends downwardly toward plate 16. Drum 22 has an axis 24, and drum 22 and cylindrical walls 14 and 18 are positioned in coaxial relationship with one another. While not shown in FIG. 1, means are positioned between cylindrical drum 22 and lower plate 16 which support drum 22 for rotation with respect to plate 16. A number of different rotary support means are currently available for such purpose, which will readily occur to those of skill in the art.

Figure 2:
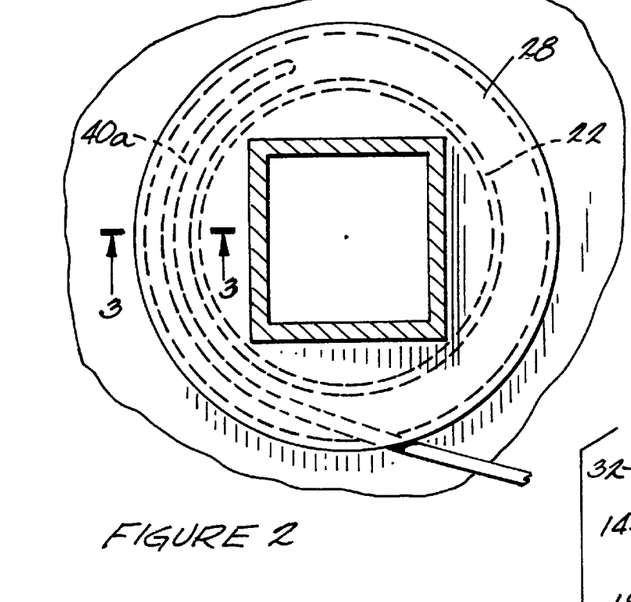
FIG. 2 is an overhead view taken in the direction of lines 2—2 of FIG. 1.
Figure 3:
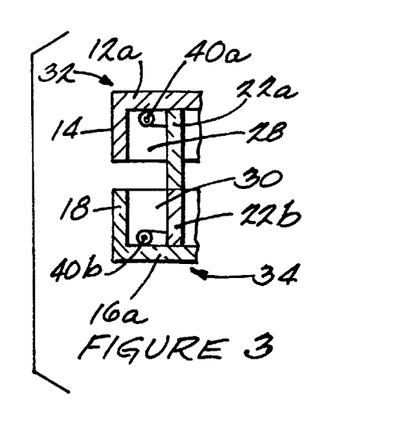
FIG. 3 is a sectional view taken along lines 3—3 of FIG. 2.

Referring further to FIG. 1, there is shown a generalized member 26 fixably mounted upon upper plate 12, which is fixably joined to cylindrical drum 22. Thus, plate 12 and member 26 rotate with drum 22, and with respect to lower plate 16 and support member 20. FIG. 1 also shows the plates 12 and 16 to have a diameter which is greater than the diameter of cylindrical drum 22. Thus, as best shown by FIGS. 2 and 3 taken together, an upper annular channel 28, having a U-shaped cross-section, is formed between cylindrical wall 14, the upper portion 22a of cylindrical drum 22, and the outer edge 12a of plate 12. Similarly, as best shown by FIG. 3, a lower annular channel 30 is formed between cylindrical wall 18, the lower portion 22b of cylindrical drum 22 and the outer edge 16a of plate 16. While not shown in FIG. 2, it is to be understood that lower annular channel 30 lies directly beneath upper annular channel 28, in uniformly spaced-apart relationship. The open sides of the two annular channels are oriented toward one another. The structure forming channel 28, i.e., wall 14, upper portion 22a, and outer edge 12a, are collectively referred to herein as upper cable guide 32. In like manner, the structure forming channel 30, i.e., wall 18, lower portion 22b, and outer edge 16a are collectively referred to herein as lower cable guide 34.

Referring again to FIG. 1, there are shown cable entry ports 15 and 19 formed through cylindrical walls 14 and 18, respectively. The ports are shown in FIG. 1 to comprise notches formed through the walls, but they alternatively could comprise apertures or the like formed therethrough. There are also shown clamps or like devices 36 and 38, joined to cable guides 32 and 34, respectively, for fixably engaging the two ends of the length of cable 40 inserted into channels 28 and 30, as described hereinafter in greater detail. Cable 40 comprises an electric power transmission cable, or segment thereof, or other cable or cable segment having some measure of resiliency. For example, cable 40 could comprise a high voltage coaxial cable of the type described above, having a diameter on the order of 0.75 inches and containing a substantial amount of rubber insulation. However, the invention is by no means limited thereto.

Because of its resilient nature, a component 40a of cable 40 readily lies along an arcuate path defined by a segment of upper channel 28, as best shown by FIG. 2. Similarly, a component 40b of cable 40 lies along an arcuate path defined by a segment of lower annular channel 30. The radius of each arcuate path is generally the radius of the annular channels. The cable component 40a comprises the portion of cable 40 extending from clamp 36, proximate to entry port 15, to a portion of cable 40 comprising a loop 40c, which is formed by and positioned between cable guides 32 and 34. Similarly, cable component 40b comprises the portion of cable 40 extending from clamp 38 to loop 40c. Thus, it will be understood that the total length of cable 40, between clamps 36 and 38, comprises the sum of the lengths of components 40a and 40b and of loop component 40c.

Figure 4:
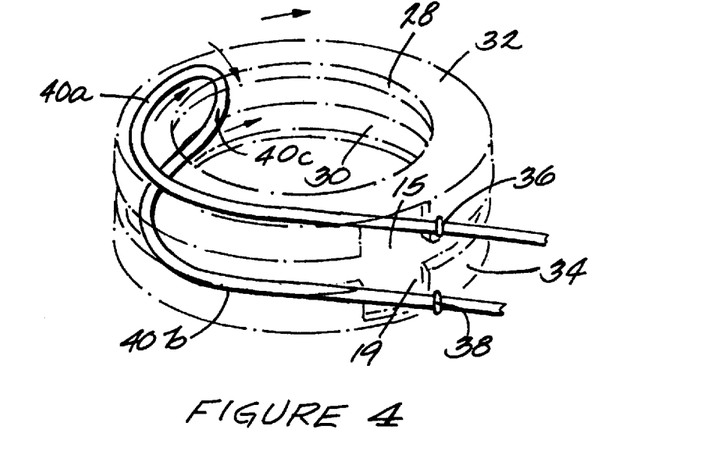
FIGS. 4 and 5 are perspective views showing the embodiment of FIG. 1 in different positions of angular rotation, with certain components thereof removed for the purpose of enhancing illustration.
Figure 5:
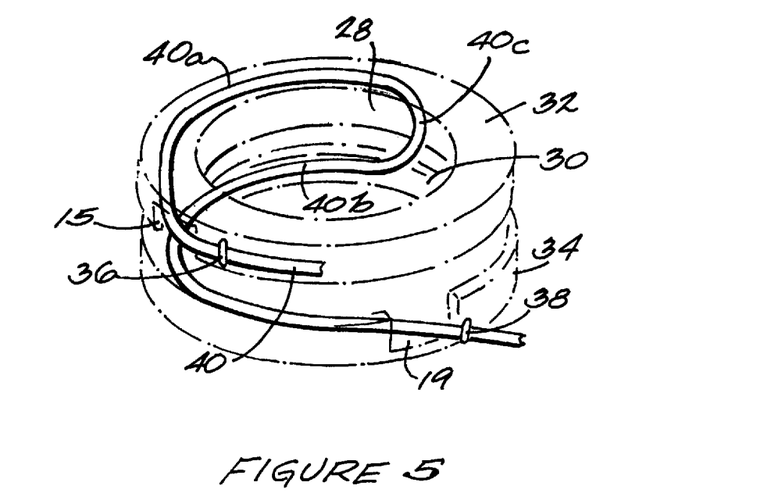

To illustrate the operation of apparatus 10, FIGS. 4 and 5 show respective components of cable 40 positioned between upper and lower cable guides 32 and 34. However, other components shown in FIG. 1, such as members 20 and 26, have been deleted from FIGS. 4 and 5, to simplify illustration.

Referring to FIG. 4, it will be seen that when upper cable guide 32 is rotated in the direction shown, i.e., a clockwise direction, the end of cable component 40a adjacent to loop 40c pushes against the loop. The loop is thereby urged downwardly, into lower channel 30. Thus, clockwise rotation of plate 12 and cable guide 32 results in transference of some of the cable 40 from upper annular channel 28 to lower annular channel 30. While the total length of cable 40 between clamps 36 and 38 remains the same, the length of upper cable component 40a diminishes, while the length of lower cable component 40b becomes correspondingly greater. This is shown by reference to FIG. 5. It is also shown that the form or configuration of loop 40c remains generally unchanged, as rotation takes place. However, the position of the loop does change, due to rotation of the loop around a path of travel defined by annular channels 28 and 30. It will be readily apparent that if upper cable guide 32 is rotated counter clockwise from the position shown therefor in FIG. 4 or FIG. 5, a portion of cable 40 will be transferred from lower channel 30 to upper channel 28, so that the length of cable component 40a will increase, and the length of cable component 40b will decrease, by the same amount.

It will be further apparent that the presence of cable 40 across the rotary joint between members 20 and 26 does not in any way interfere with rotation of member 26 relative to member 20. Moreover, respective components of cable 40 remain compact and substantially enclosed between cable guides 32 and 34. Thus, there is comparatively little chance that cable 40 will snag or become entangled with persons or objects which are proximate to the rotary joint between members 20 and 26. If cable 40 is an electric cable, two other cables, respectively joined to fixed member 20 and rotatable member 26, can be electrically coupled to the ends of cable 40 held in place by clamps 38 and 36. Cable 40 would thereby provide a transmission path across the rotary joint between members 20 and 26, for electric power or signals. Alternatively, and completely within the scope of the invention, cable 40 could comprise a segment of an integral cable, positioned between two other cable segments which were fixably joined to members 20 and 26, respectively.

Figure 6:
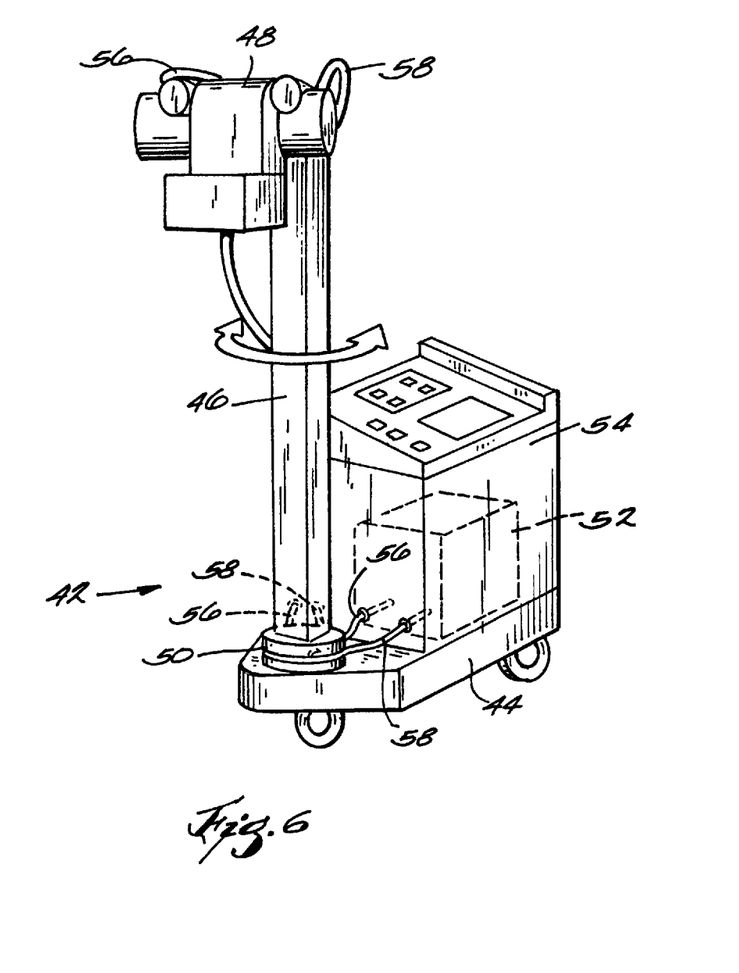
FIG. 6 is a perspective view showing an X-ray imaging system provided with a second embodiment of the invention.

Referring to FIG. 6, there is shown a mobile X-ray unit 42 usefully employing an embodiment of the invention. Unit 42 may be similar to the aforementioned AMX-4 X-ray unit, but is not limited thereto. Unit 42 generally includes a carriage or platform 44 provided with wheels, whereby unit 42 may be readily moved or transported over a floor or other supportive horizontal surface (not shown). A column 46 extending upward from platform 44 supports a conventional X-ray tube 48, which produces a beam of X-radiation for acquiring X-ray exposures of a patient or other subject (not shown). Column 46 is mounted for rotation relative to platform 44 about a vertical axis, to position X-ray tube 48 to project the X-ray beam in the desired orientation with respect to a patient. Usefully, column 46 may rotate through a specified angular range, in both clockwise and counter-clockwise directions, from a zero degree reference position.

In order to drive tube 48 to produce X-rays, a high voltage potential, on the order of 75,000 volts, must be applied between the tube anode and cathode (not shown). Such voltage is provided by an X-ray tube generator 52, contained in a housing 54 mounted on platform 44, together with other components required for operation of X-ray unit 42. The tube driving voltage is coupled from generator 52 to the anode and cathode of tube 48 through high voltage coaxial anode and cathode cables 56 and 58, respectively. Each of such cables usefully comprises a resilient cable such as cable 40, described above. Cables 56 and 58 are coupled from housing 54 along platform 44, and up through column 46 to tube 48. Thus, both of the cables must cross the rotary joint between platform 44 and column 46, without interfering with the rotation of column 46. Accordingly, a cable routing apparatus 50, comprising a further embodiment of the invention, is positioned between platform 44 and column 46. Apparatus 50 operates, as described hereinafter in further detail, to route or direct both cables 56 and 58 across the rotary joint.

Figure 7:
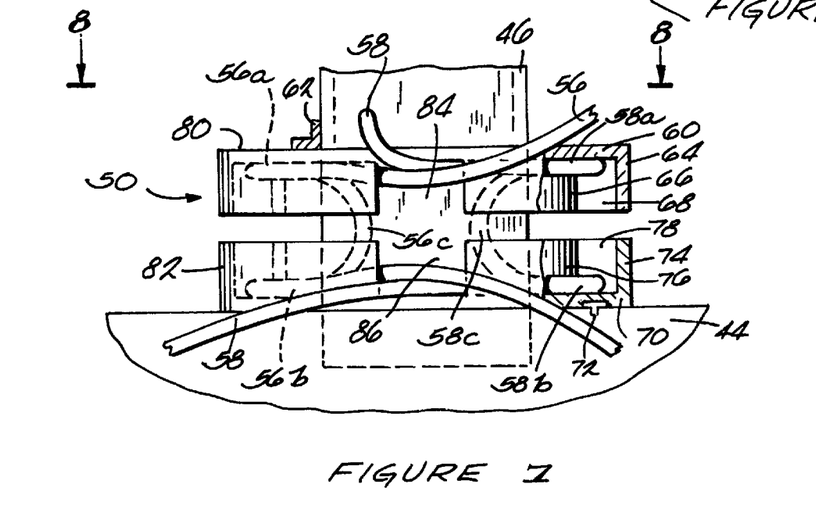
FIG. 7 is a perspective view with a section broken away showing the embodiment of FIG. 6 in greater detail.

Referring to FIG. 7, there is shown column 46 journaled for rotation about its vertical axis by means of bearings or the like (not shown) located in platform 44, below the surface thereof. (The lower-most portion of column 46, which contacts the bearings, may usefully be provided with a circular cross-section rather than the square or rectangular cross-section shown in certain Figures). In one embodiment, column 46 is manually rotated. Alternatively, power drive means (not shown) could be located in or beneath platform 44 to automatically rotate column 46.

Figure 8:
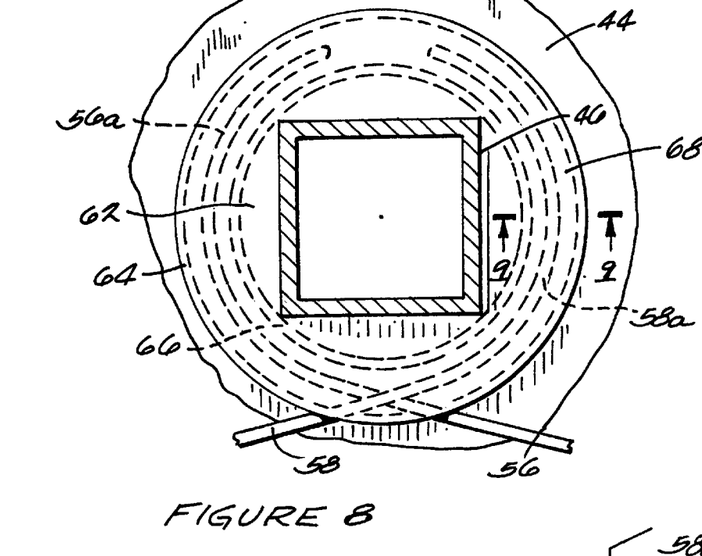
FIG. 8 is an overhead view taken in the direction of lines 8—8 of FIG. 7.
Figure 9:
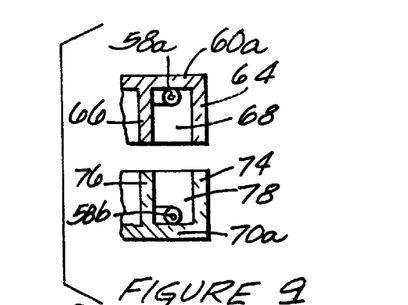
FIG. 9 is a sectional view taken along lines 9—9 of FIG. 8.

Referring further to FIG. 7, there is shown apparatus 50 including an upper circular plate 60 positioned around column 46, in coaxial relationship therewith. An aperture is formed through the center of plate 60, to enable column 46 to pass therethrough. Plate 60 is fixably joined to column 46, for rotation therewith, by any suitable means. For example, plate 60 may be welded to column 46, or may be joined thereto by means of brackets 62 or the like. A cylindrical wall 64 is joined around the outer edge of the circumference of plate 60, and extends downwardly therefrom, as viewed in FIG. 7. A second cylindrical wall 66, having a selectively smaller diameter than cylindrical wall 64, is likewise joined to the underside of plate 60, in coaxial relationship therewith, and extends downwardly therefrom. Thus, as best shown in FIGS. 8 and 9, the outer edge 60a of plate 60 and cylindrical walls 64 and 66 collectively form an upper annular channel 68, having a U-shaped cross-section.

FIG. 7 further shows apparatus 50 provided with a lower circular plate 70, which is fixably joined to platform 44, such as by means of bolts 72. In like manner with upper circular plate 60, plate 70 is positioned in coaxial relationship with column 46, and an aperture is formed in the center of plate 70, so that column 46 can pass therethrough. The diameter of circular plate 70 is identical to the diameter of plate 60, and a cylindrical wall 74 is joined around the circumference of plate 70, to extend upwardly therefrom, as viewed in FIG. 7. A second cylindrical wall 76, having a diameter equal to cylindrical wall 66, is joined to the upper side of plate 70, in coaxial relationship therewith, and extends upwardly therefrom. Thus, as best shown FIG. 9, the outer edge 70a of platform 70 and cylindrical walls 74 and 76 collectively form a lower annular channel 78, having a U-shaped cross-section. While not shown in FIG. 8, it is to be understood that lower annular channel 78 lies directly beneath upper annular channel 68, in uniformly spaced-apart relationship. The open sides of the two annular channels are oriented toward one another. The structure forming channel 68, i.e., plate 60 and cylindrical walls 64 and 66 are collectively referred to herein as upper cable guide 80. In like manner, the structure forming channel 78, i.e., plate 70 and cylindrical walls 74 and 76 are collectively referred to herein as lower cable guide 82. Upper cable guide 80 is provided with a cable entry port 84, and lower cable guide 82 is provided with a cable entry port 86.

In the embodiment described above in connection with FIGS. 1–5, only a single cable or cable segment is shown to be routed across the rotary joint. However, at any given time the cable occupies only an arcuate portion or segment of annular channels 28 and 30. Moreover, the position of the cable shifts, as guide channel 68 is rotated. Thus, in accordance with the invention, it has been recognized that an embodiment, such as apparatus 50, can be used in connection with more than one cable at the same time. Accordingly, referring to FIGS. 7 and 8, there are shown segments of both anode cable 56 and cathode cable 58 inserted through entry ports 84 and 86 into annular channels 68 and 78, between cable guides 80 and 82. The inserted segment of cable 56 comprises an upper component 56a, lying along an arcuate portion of upper channel 68, a lower component 56b lying along an arcuate portion of lower channel 78, and a loop component 56c extending between the ends of components 56a and 56b. Similarly, cable segment 58 comprises an upper component 58a, a lower component 58b, and a loop component 58c. Cable segments 56 and 58 are generally positioned to lie along opposing sides of the annular channels 68 and 78. It is to be noted that clamps or other means for joining respective ends of the cable segments to their corresponding cable guides have been deleted from FIG. 7.

Figure 10:
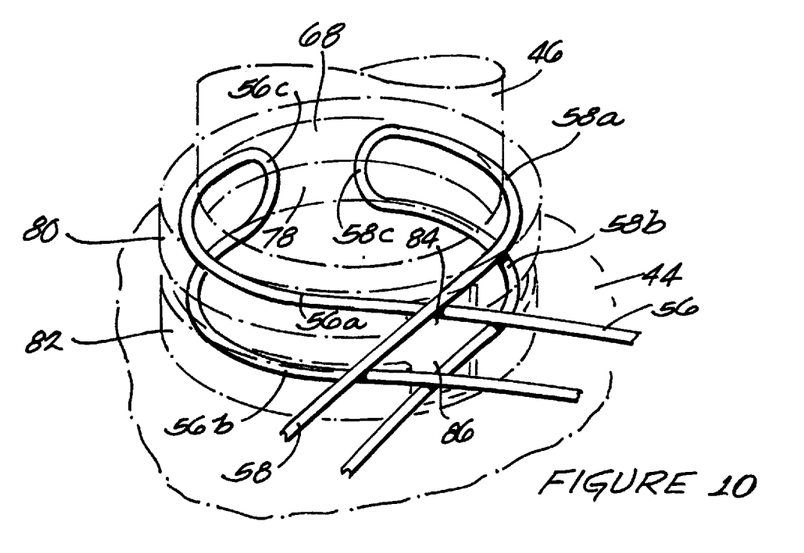
FIGS. 10 and 11 are perspective views showing the embodiment of FIGS. 5 and 6 in different positions of angular rotation.
Figure 11:
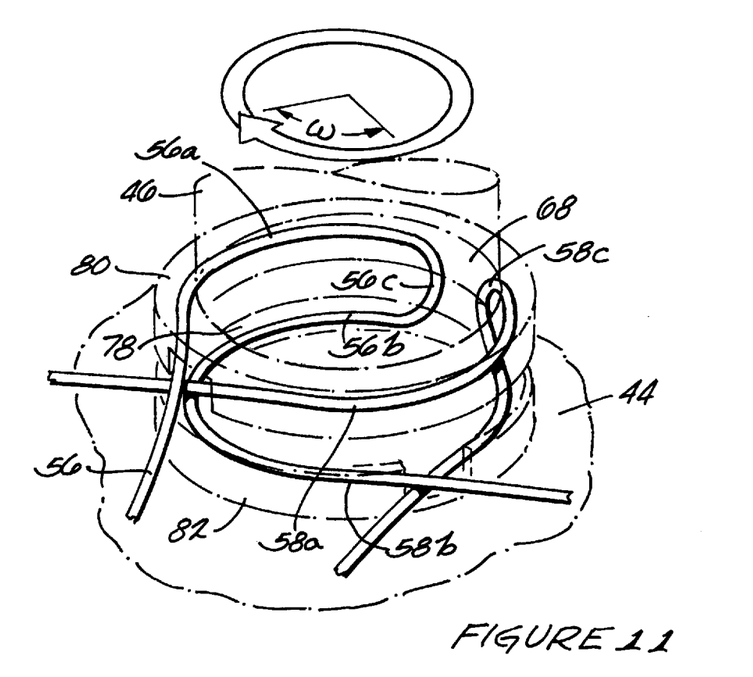

Referring to FIGS. 10 and 11, there is shown upper cable guide 80 in two different rotational positions with respect to lower cable guide 82. More particularly, FIG. 11 shows cable guide 80 rotated in a counterclockwise direction, through the angle ω, from the position shown therefore in FIG. 10. Referring to the two figures together, it is seen that as cable guide 80 rotates in a counterclockwise direction, both loops 56c and 58c rotate counterclockwise, around an arcuate path defined by channels 68 and 78. The length of cable component 56a decreases, and lower component 56b increases by the same amount. Similarly, upper component 58a increases and lower component 58b decreases. Thus, it is seen that column 46, together with cable guide 80, can rotate with respect to platform 44, without either interfering with or being obstructed by the segments of cables 56 and 58 contained within apparatus 50. It is anticipated that by judicious selection of certain parameters, such as the radius of annular channels 68 and 78, and the total lengths of the cable segments inserted into apparatus 50, column 46 can rotate through a selected angular range, such as 270°, in both clockwise and counterclockwise directions, from a zero angle reference.

Further modifications could route numbers of cables in excess of two across a rotary joint, depending on parameters such as the angular range of rotation and the radii of the annular channels. Also, a cable lying along the cable guides could in fact comprise several electrical conductors, either gathered in bundles or unbundled.

Obviously, many other modifications and variations of the present invention are possible in light of the above teachings. It is therefore to be understood that within the scope of the disclosed concept, the invention may be practiced otherwise than as specifically described.

What is claimed is:

1. In an arrangement wherein a first member is supported for rotation with respect to a second member, apparatus for routing a resilient cable of specified length across a joint between said first and second members, comprising:

first guide means disposed to rotate with said first member for guiding a first component of said cable along a first arcuate path having a specified radius, the length of said first cable component disposed to vary as said first member rotates;

second guide means in fixed relation with said second member for guiding a second component of said cable along a second arcuate path having a specified radius, that length of said second cable component disposed to vary in inverse relation to said variation of the length of said first cable component;

said first and second guide means comprise first and second arcuate channels, respectively, each of said arcuate channels having a specified radius and an open side;

means for mounting said first and second guide means to orient the open sides thereof toward each other, and to provide a spacing therebetween which is selected to accommodate a third component of said cable which comprises a loop of specified configuration extending between said first and second cable components; and means for joining one end of said cable in fixed relationship with said first guide means, and for joining the opposing end of said cable in fixed relationship with said second guide means.

2. The apparatus of claim 1 wherein:

said first and second arcuate channels are of sufficient dimensions to accommodate the maximum lengths of said first and second cable components, respectively.

3. The apparatus of claim 2 wherein:

a port is formed in each of said arcuate channels, each of said ports being sized to allow an end of said cable to pass therethrough.

4. The apparatus of claim 2 wherein:

said first and second arcuate channels comprise segments of first and second annular channels, respectively, said first and second annular channels being supported in spaced-apart relationship with one another.

5. The apparatus of claim 4 wherein:

a plurality of said cables are positioned to lie along said first and second arcuate channels at the same time.

6. The apparatus of claim 4 wherein:

two different cables are positioned to lie along said first and second arcuate channels at the same time, said cables occupying different arcuate segments of said channels at a given time.

7. In an arrangement wherein a first member is supported for rotation with respect to a second member, apparatus for transmitting electric power of specified voltage across a rotary joint between said first and second members comprising:

a selected number of resilient electric transmission cables, each of said cables disposed to transmit electric power of said specified voltage;

first guide means disposed to rotate with said first member for guiding first components of each of said cables along respectively corresponding first arcuate paths, the length of each of said first cable components disposed to vary as said first member rotates;

second guide means in fixed relation with said second member for guiding second components of each of said cables along respectively corresponding second arcuate paths, the length of each of said second cable components disposed to vary in inverse relation to the length of a corresponding first cable component;

said first and second guide means comprise first and second arcuate channels, respectively, each of said arcuate channels having a specified radius and an open side;

means for mounting said first and second guide means to orient the open sides thereof toward each other, and to provide a spacing therebetween which is selected to accommodate a third component of each of said cables, each of said third components comprising a loop extending between corresponding first and second cable components; and means for joining one end of each of said cables in fixed relationship with said first guide means, and for joining the opposing end of each of said cables in fixed relationship with said second guide means.

8. The apparatus of claim 7 wherein:

said first and second arcuate channels comprise segments of first and second annular channels, respectively, said first and second annular channels being supported in spaced-apart relationship with one another.

9. The apparatus of claim 8 wherein:

each of said cables comprises a high voltage coaxial cable.

10. The apparatus of claim 9 wherein:

said apparatus comprises two of said cables.

11. In an arrangement wherein a first member is supported for rotation with respect to a second member, apparatus for transmitting electric power of specified voltage across a rotary joint between said first and second members comprising:

a plurality of electric transmission cables, each of said cables disposed to transmit electric power of said specified voltage;

a first cable guide disposed to rotate with said first member for guiding first components of each of said cables along respectively corresponding portions of a common first annular path defined by said first cable guide, the length of each of said first cable components disposed to vary as said first member rotates;

a second cable guide in fixed relation with said second member for guiding second components of each of said cables along respectively corresponding portions of a common second annular path defined by said second cable guide, the length of each of said second cable components disposed to vary in inverse relation to the length of a corresponding first cable component, second guide positioned with respect to said first to provide a spacing therebetween to accommodate a third component of each of said cables comprising a loop of specified configuration, each of said loops extending between corresponding first and second cable components; and fasteners for joining one end of each of said cables in fixed relationship with said first guide, and for joining the opposing end of each of said cables in fixed relationship with said second guide.

12. The apparatus of claim 11 wherein:

said first and second guides comprise first and second annular channels, respectively; and each of said cables is of selected resiliency so that rotation of said first member results in transfer of a portion of each of said cables from one of said annular channels to the other.

13. The apparatus of claim 12 wherein:

each of said cables comprises a high voltage coaxial cable.

14. The apparatus of claim 13 wherein:

said apparatus comprises two of said cables.

* * * * *